United States Patent [19]
Zimmerman

[11] 3,962,581
[45] June 8, 1976

[54] INFRA-RED CONSISTENCY METER

[75] Inventor: William E. Zimmerman, Covington, Va.

[73] Assignee: Westvaco Corporation, New York, N.Y.

[22] Filed: Oct. 6, 1975

[21] Appl. No.: 619,677

[52] U.S. Cl. .............................. 250/341; 250/574; 356/51; 356/103
[51] Int. Cl.² .................. G01N 21/00; G01N 21/26; G01N 21/34; G01N 21/46
[58] Field of Search ............... 250/212, 574, 222 PC, 250/341; 356/103, 51

[56] References Cited
UNITED STATES PATENTS

| | | | |
|---|---|---|---|
| 3,177,757 | 4/1965 | Polyanyi | 250/574 |
| 3,564,262 | 2/1971 | Hach | 250/574 |
| 3,854,045 | 12/1974 | Breuer et al. | 250/341 |

Primary Examiner—Alfred E. Smith
Assistant Examiner—T. N. Grigsby
Attorney, Agent, or Firm—W. Allen Marcontell; Richard L. Schmalz

[57] ABSTRACT

The consistency of solid particles in an aqueous fluid suspension may be measured over the range of 0.20 to 20% from the magnitude of electrical power generated by a 0.35 to 1.05 micron light spectrum responsive silicon photocell that is energized by a low, constant power incandescent light source. Light from the source is reflected from the suspension flow stream. The reflected light is filtered to block passage of wavelengths less than 0.70 microns to the photocell. Angular disposition of the photocell relative to the light path is adjusted to emphasize either a direct relationship between cell power and consistency changes or an inverse relationship thereof.

12 Claims, 2 Drawing Figures

INFRA-RED CONSISTENCY METER

BACKGROUND OF THE INVENTION

1. Field Of The Invention

The present invention relates to the measurement of solid particle consistency in an aqueous flow stream. More particularly, the present invention relates to the measurement wood fiber consistency in a pulp stock flow stream.

2. Description Of The Prior Art

In many industrial processes, a finely divided particulate solid will be suspended in an aqueous medium as a slurried mixture for transport through a multiplicity of process steps. Often, it is necessary to know, to a high degree of accuracy, the solid-to-liquid ratio of such mixtures. This ratio, or some mathematical permutation thereof, is characterized by the wood pulp and papermaking industry as consistency.

The direct measurement of consistency is presently accomplished by numerous techniques depending on the particular application. A low consistency of 0.20 to 1.0 percent has been measured optically by sensing the magnitude of a particular frequency light from a constant energy emissive source that penetrates the slurry flow stream between two transparent windows in a carrier conduit. U.S. Pat. No. 3,322,960 describes apparatus having utility for this purpose.

Pulp slurry consistencies in the range of 0.50 to 5.0 percent may also be deduced from the measurement of torque required to drive, at a constant rotational speed, an axially rotating rod immersed in the slurry, said rod having whisker wires projecting normally therefrom. U.S. Pat. No. 3,488,995 describes apparatus of this type.

In the higher consistency ranges, reliable consistency measurement may be deduced from the total slurry mass shielding of beta ray transmissivity relative to that caused by the pure fluid carrier. Similarly, high consistency measurement may be obtained from the degree of electrical conductivity between two electrodes penetrating the mixture.

When the subject of measurement is a slurry of wood pulp, coagulative properties of the pulp create particular problems with such prior art techniques of low consistency measurement. Because of the low light transmissivity of a 0.50 percent slurry, windowed instrument conduits must be narrow and connected for parallel flow with the main process flow stream. Accordingly, unrepresentative samples are presented to the measured light path. Furthermore, because of the relatively small dimensions, the sample flow stream tends to clog with flocs of pulp.

Similarly, because of pulp adherence to a rotating rod and wires projecting therefrom, erroneous indications of consistency will be given by this technique.

It is, therefore, an object of the present invention to measure a low consistency wood pulp slurry by means invulnerable to prior art error sources.

It is also an object of the present invention to photometrically measure a low consistency slurry within a large diameter, main flow line carrier of such slurry.

Another object of the present invention is to measure a low consistency slurry without need of passing a light beam completely through the slurry flow stream.

SUMMARY OF THE INVENTION

These and other objects of the present invention are accomplished by means of a 0.350 to 1.05 micron light sensitive silicon photocell secured to a single, transparent window in a slurry conduit behind a 0.70 micron filter of shorter wave-lengths. The cell is energized by a low power incandescent light source positioned laterally of and behind the silicon cell relative to the exterior window plane. By selectively adjusting the plane of the photocell relative to the window plane, single reflective incidence light impinging on the photocell may be emphasized for a direct, cell power output-to-consistency relationship. Opposite adjustment of the photocell angle will achieve an inverse relationship between power output and consistency by emphasizing the receipt of multiple reflected light. Wood pulp consistencies over the range of 0.20 to 20% may be measured in this manner.

BRIEF DESCRIPTION OF THE DRAWING

Relative to the two figures of the drawing wherein like reference characters designate like or similar elements.

DESCRIPTION OF THE PREFERRED EMBODIMENT

Figure 1:
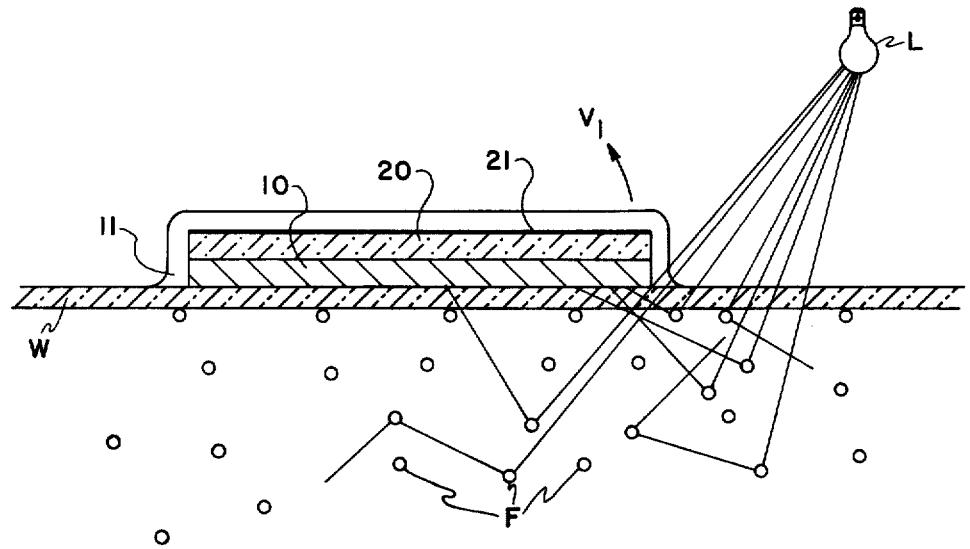
FIG. 1 illustrates a sectional view of the invention disposed on the window of a low consistency slurry carrier conduit for direct power-to-consistency change response.

Relative to both figures of the drawing, window W is a transparent barrier wall of a flow conduit carrying a low consistency slurry of wood pulp fibers F.

Placed directly against the exterior surface plane of window W is a near infra-red light filter 10 having properties such that only wave-lengths of light greater than approximately 0.70 microns are permitted to pass. Shorter light wave-lengths are blocked thereby.

Next to the filter 10, on the opposite side thereof from window W, is a silicon photocell 20 having a spectral response of 0.350 to 1.05 microns disposed with the light sensitive face thereof against the filter. An opaque backing 21 for the photocell provides an absolute shield of all light incident upon the reverse plane thereof.

A coating 11 of Goodyear Pliobond, for example, secures and atmospherically seals, the photocell filter unit to the window W.

A small, 15 watts for example, substantially constant incandescent light source L emits sufficient light energy for photocell excitation. Light L may be positioned approximately 1 inch laterally of the most proximate photocell edge and approximately one inch spaced from the exterior face of window W.

Successful use of the aforedescribed elements is largely predicated on the orientation of the photocell relative to the plane of window W; assuming a fixed position for light source L. Such orientation constitutes a calibration procedure whereby one of two reflective light energy paths are followed from the light source L to the photocell.

The first such energy path is illustrated by FIG. 1 wherein the photocell unit is angularly displaced relative to the plane of window W in the direction represented by vector $V_1$. Mechanically, this is accomplished by lifting the edge of the photocell unit most proximate of the light L from the window surface prior to sealing. The correct angular setting for a particular installation will be that at which a maximum photocell power increase is occasioned by a given increased consistency change.

Figure 2:
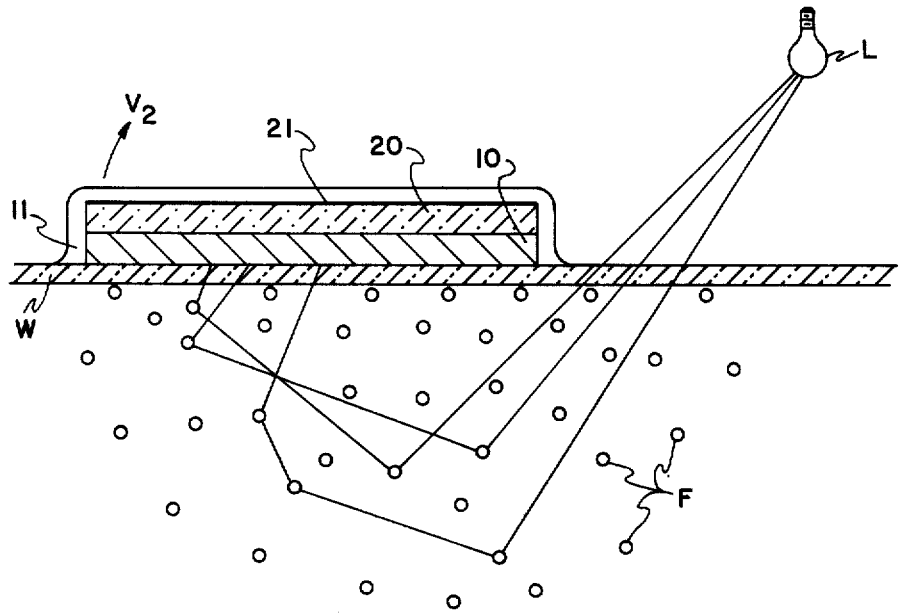
FIG. 2 illustrates a sectional view of the invention disposed on the window of a low consistency slurry carrier conduit for inverse power-to-consistency change response.

Relative to FIG. 2, the second calibration technique of the subject invention is essentially the opposite of the first whereby the most remote edge of the photocell unit is lifted in the direction of vector $V_2$ to a position whereat the photocell power output falls to a minimum value as a consequence of a given increase in consistency.

Therefore, according to the FIG. 1 calibration technique, a direct, power output-to-consistency, change may be established whereas in the FIG. 2 technique, an inverse power-consistency relationship is emphasized.

Although an explanation of the aforedescribed operation of my invention will be attempted as follows, it should be understood that such explanation is merely conjecture that seems responsive to the known physical facts.

Since a wood pulp slurry is a suspension of light reflective but opaque fibers in a substantially transparent water vehicle, the mixture responds as a translucent body. Consequently, light directed thereinto is reflected and dispersed as a function of the concentration of opaque particles suspended therein. Accordingly, a certain percentage of total light incident upon such a translucent body is reflected at or near the surface thereof by only one or at most, a very few incidents of reflection. When the plane of the photocell 20 is, therefore, adjusted in the manner illustrated by FIG. 1, it is brought into greater alignment with such direct light reflections. Although the percentage of single reflective incidence light is unchanged for a given consistency value, the percentage of the total of such light rebounding from the entire area illuminated by source L, as received by photocell 20, may be regulated by the photocell angle. In other words, the photocell "sees" more light from a given consistency value and if the consistency is increased, the photocell receives proportionately more light.

In the FIG. 2 case, light received by the photocell must travel a more tortuous course before reaching the photocell face. Most of the illuminating light which penetrates the flow stream is absorbed thereby without consequence on the photocell. However, a small percentage thereof is turned back into the photocell plane after reflection from a multiplicity of surfaces. For this reason, if the flow stream consistency increases, a proportionately smaller quantity of such transmitted light reaches the photocell. Accordingly, the cell power output changes inversely with changes in flow stream consistency.

Those skilled in the art will recognize that changes in the slurry brightness will also affect the magnitude of photocell power output. In recognition of the fact that wood pulp brightness can and does change from time to time for diverse reasons, the near infra-red filter 10 is interposed between the photocell face and the conduit window W. It has been found that the reflectivity of light wave-lengths greater than 0.70 microns from suspended particles of wood fiber is substantially unaffected by the superficial color and texture characteristics of the particles. Consequently the magnitude of light within this spectral range reflected from a substantially constant emission source is substantially constant notwithstanding brightness changes.

Having fully described the preferred embodiments of my invention, I claim:

1. A method of measuring the consistency of opaque particles suspended in a translucent, fluidized slurry, said method comprising:
    A. Illuminating a substantially homogenous flow stream of said slurry with a white light source of substantially constant power;
    B. Filtering light originated from said source and reflected from said flow stream to permit only the substantial passage of wave-lengths greater than 0.70 microns;
    C. Energizing with said filtered light a photocell that is responsive to wave-lengths within the spectrum of 0.70 microns to 1.05 microns;
    D. Calibrating the electrical energy generation of said photocell relative to a known consistency of said slurry.

2. A method of measuring the consistency of a fluidized slurry as described by claim 1 wherein said photocell is shielded from light having direct incidence from said source to said photocell.

3. A method of measuring the consistency of a fluidized slurry as described by claim 1 wherein said photocell energy generation is calibrated to respond with a direct proportionality to changes in said slurry consistency.

4. A method of measuring the consistency of a fluidized slurry as described by claim 1 wherein said photocell energy generation is calibrated to respond with an inverse proportionality to changes in said slurry consistency.

5. Apparatus for measuring the consistency of opaque particles suspended in a translucent, fluidized slurry, said apparatus comprising:
    A. A white light source of substantially constant power disposed to illuminate a portion of a substantially homogenous flow stream of said slurry;
    B. A photocell that is energized by light wave-lengths within the spectrum of 0.70 microns to 1.05 microns disposed between said light source and said flow stream;
    C. A light shield positioned to block the direct incidence of all light from said source into said photocell; and,
    D. A microns emanating filter positioned between said photocell and said flowstream to pass only wave-lengths of light greater than 0.70 micron-semanating from said source and reflected from said flow stream.

6. Apparatus as described by claim 5 wherein said photocell is of the silicon type having power generation response to wave-lengths substantially within the spectrum of 0.35 to 1.05 microns.

7. Apparatus as described by claim 5 wherein said photocell is oriented relative to said light source to provide a power generation response that is directly proportional to changes in the consistency of said flow stream.

8. Apparatus as described by claim 5 wherein said photocell is oriented relative to said light source to provide a power generation response that is inversely proportional to changes in the consistency of said flow stream.

9. Apparatus for measuring the consistency of a wood pulp slurry comprising:
   A. A substantially constant power white light source positioned adjacent a substantially homogenous flow stream of said slurry to illuminate a portion thereof;
   B. A photocell having power generation response within the light wave-length spectrum of 0.70 to 1.05 microns, said photocell being positioned more proximate of said flow stream illuminated portion than said light source;
   C. A light shield to block the direct incidence of all light from said source into said photocell; and
   D. A light filter positioned between said photocell and said illuminated portion to pass only wavelengths of light greater than 0.70 microns emanating from said source and reflected from said flow stream.

10. Apparatus as described by claim 9 wherein said photocell is of the silicon type having a power generation response to wave-length substantially within the spectrum of 0.35 to 1.05 microns.

11. Apparatus as described by claim 9 wherein said photocell is oriented relative to said light source to provide a power generation response that is directly proportional to changes in the consistency of said flow stream.

12. Apparatus as described by claim 9 wherein said photocell is oriented relative to said light source to provide a power generation response that is inversely proportional to changes in the consistency of said flow stream.

* * * * *

UNITED STATES PATENT OFFICE
CERTIFICATE OF CORRECTION

Patent No. 3,962,581  Dated June 8, 1976

Inventor(s) William E. Zimmerman

It is certified that error appears in the above-identified patent and that said Letters Patent are hereby corrected as shown below:

Column 4, line 50, "microns emanating" should read -- light --;

lines 52 and 53, "micron-semanating" should read -- microns emanating --

Signed and Sealed this

Nineteenth Day of October 1976

[SEAL]

Attest:

RUTH C. MASON
*Attesting Officer*

C. MARSHALL DANN
*Commissioner of Patents and Trademarks*